(12) United States Patent
Zuberi et al.

(10) Patent No.: US 8,680,138 B2
(45) Date of Patent: Mar. 25, 2014

(54) ORGANIC SEMICONDUCTORS

(75) Inventors: Tania Zuberi, Middlesex (GB); Sheena Zuberi, Middlesex (GB)

(73) Assignee: Cambridge Display Technology Limited, Cambridgeshire (GB)

( * ) Notice: Subject to any disclaimer, the term of this patent is extended or adjusted under 35 U.S.C. 154(b) by 157 days.

(21) Appl. No.: 13/129,348

(22) PCT Filed: Nov. 27, 2009

(86) PCT No.: PCT/GB2009/002738
§ 371 (c)(1),
(2), (4) Date: Jun. 21, 2011

(87) PCT Pub. No.: WO2010/061178
PCT Pub. Date: Jun. 3, 2010

(65) Prior Publication Data
US 2011/0233535 A1 Sep. 29, 2011

(30) Foreign Application Priority Data
Nov. 28, 2008 (GB) .................................. 0821705.1

(51) Int. Cl.
*A61K 31/381* (2006.01)
*C07D 409/14* (2006.01)

(52) U.S. Cl.
USPC ............................................ 514/443; 549/4

(58) Field of Classification Search
USPC ............................................ 514/443; 549/4
See application file for complete search history.

(56) References Cited

U.S. PATENT DOCUMENTS

| | | |
|---|---|---|
| 2003/0021912 A1 | 1/2003 | Farrand et al. |
| 2003/0042471 A1 | 3/2003 | Giles et al. |
| 2004/0230021 A1 | 11/2004 | Giles et al. |
| 2007/0112171 A1 | 5/2007 | Li et al. |

FOREIGN PATENT DOCUMENTS

| | | |
|---|---|---|
| EP | 1 993 105 | 11/2008 |
| WO | WO-99/12989 A1 | 3/1999 |
| WO | WO-2005/111045 A1 | 11/2005 |
| WO | WO-2006/031893 A2 | 3/2006 |

OTHER PUBLICATIONS

Miguel et al., "Planar β-Linked Oligothiophenes Based on Thieno[3,2-*b*]thiophene and Dithieno[3,2-*b*:2',3'-*d*]thiophene Fused Units," *Org. Lett.*, 9(6):1005-1008 (2007).
Morrison et al., "Preparation of Bis(dithienothiophene) Derivatives for Organic Thin Film Transistors," *Syn. Met.*, 102:987-988 (1999).
Wang et al., "Solvent Effects and Multiple Aggregate States in High-Mobility Organic Field-Effect Transistors Based on Poly(bithiophene-*alt*-thienothiophene)," *Appl Phys. Lett.*, 93:162103 (2008).
International Preliminary Report on Patentability for Application No. PCT/GB2009/002738, dated May 31, 2011.
International Search Report and Written Opinion for Application No. PCT/GB2009/002738, dated Feb. 22, 2010.
Search Report for Application No. GB0821705.1, dated Mar. 19, 2009.

*Primary Examiner* — Taofiq A Solola
(74) *Attorney, Agent, or Firm* — Marshall, Gerstein & Borun LLP

(57) ABSTRACT

A soluble oligomeric compound for forming an organic thin film transistor, has repeat units comprising two or more fused thiophene residues. The repeat units comprise the structure:

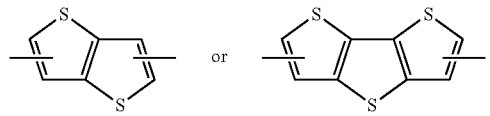

The compound may include two or more terminating groups comprising solvating groups. A solution of the material can be used to form a thin film transistor by ink jet printing.

10 Claims, 2 Drawing Sheets

ORGANIC SEMICONDUCTORS

The present invention relates generally to organic semiconductors and in particular to organic semiconductors for forming part of a thin film transistor.

BACKGROUND TO THE INVENTION

Transistors can be divided into two main types: bipolar junction transistors and field-effect transistors. Both types share a common structure comprising three electrodes with a semiconductive material disposed there between in a channel region. The three electrodes of a bipolar junction transistor are known as the emitter, collector and base, whereas in a field-effect transistor the three electrodes are known as the source, drain and gate. Bipolar junction transistors may be described as current-operated devices as the current between the emitter and collector is controlled by the current flowing between the base and emitter. In contrast, field-effect transistors may be described as voltage-operated devices as the current flowing between source and drain is controlled by the voltage between the gate and the source.

Transistors can also be classified as p-type and n-type according to whether they comprise semiconductive material which conducts positive charge carriers (holes) or negative charge carriers (electrons) respectively. The semiconductive material may be selected according to its ability to accept, conduct, and donate charge. The ability of the semiconductive material to accept, conduct and donate holes or electrons can be enhanced by doping the material.

For example, a p-type transistor device can be formed by selecting a semiconductive material which is efficient at accepting, conducting, and donating holes, and selecting a material for the source and drain electrodes which is efficient at injecting and accepting holes from the semiconductive material. Good energy-level matching of the Fermi-level in the electrodes with the HOMO level of the semiconductive material can enhance hole injection and acceptance. In contrast, an n-type transistor device can be formed by selecting a semiconductive material which is efficient at accepting, conducting, and donating electrons, and selecting a material for the source and drain electrodes which is efficient at injecting electrons into, and accepting electrons from, the semiconductive material. Good energy-level matching of the Fermi-level in the electrodes with the LUMO level of the semiconductive material can enhance electron injection and acceptance.

Transistors can be formed by depositing the components in thin films to form a thin film transistor (TFT). When an organic material is used as the semiconductive material in such a device, it is known as an organic thin film transistor (OTFT).

OTFTs may be manufactured by low cost, low temperature methods such as solution processing. Moreover, OTFTs are compatible with flexible plastic substrates, offering the prospect of large-scale manufacture of OTFTs on flexible substrates in a roll-to-roll process.

With reference to FIG. 1, the general architecture of a bottom-gate organic thin film transistor (OTFT) comprises a gate electrode 12 deposited on a substrate 10. An insulating layer 11 of dielectric material is deposited over the gate electrode 12 and source and drain electrodes 13, 14 are deposited over the insulating layer 11 of dielectric material. The source and drain electrodes 13, 14 are spaced apart to define a channel region therebetween located over the gate electrode 12. An organic semiconductor (OSC) material 15 is deposited in the channel region for connecting the source and drain electrodes 13, 14. The OSC material 15 may extend at least partially over the source and drain electrodes 13, 14.

Alternatively, it is known to provide a gate electrode at the top of an organic thin film transistor to form a so-called top-gate organic thin film transistor. In such an architecture, source and drain electrodes are deposited on a substrate and spaced apart to define a channel region therebetween. A layer of an organic semiconductor material is deposited in the channel region to connect the source and drain electrodes and may extend at least partially over the source and drain electrodes. An insulating layer of dielectric material is deposited over the organic semiconductor material and may also extend at least partially over the source and drain electrodes. A gate electrode is deposited over the insulating layer and located over the channel region.

An organic thin film transistor can be fabricated on a rigid or flexible substrate. Rigid substrates may be selected from glass or silicon and flexible substrates may comprise thin glass or plastics such as poly(ethylene-terephthalate) (PET), poly(ethylene-naphthalate) PEN, polycarbonate and polyimide.

Exemplary solvents for compounds of the present invention include benzenes substituted with one or more alkyl or halogen groups for example toluene, xylene; and tetralin. Preferred solution deposition techniques include spin coating and ink jet printing. Other solution deposition techniques include dip-coating, roll printing and screen printing.

The length of the channel defined between the source and drain electrodes may be up to 500 microns, but preferably the length is less than 200 microns, more preferably less than 100 microns, most preferably less than 20 microns.

The gate electrode can be selected from a wide range of conducting materials for example a metal (e.g. gold) or metal compound (e.g. indium tin oxide). Alternatively, conductive polymers may be deposited as the gate electrode. Such conductive polymers may be deposited from solution using, for example, spin coating or ink jet printing techniques and other solution deposition techniques discussed above.

The insulating layer comprises a dielectric material selected from insulating materials having a high resistivity. The dielectric constant, k, of the dielectric is typically around 2-3 although materials with a high value of k are desirable because the capacitance that is achievable for an OTFT is directly proportional to k, and the drain current $I_D$ is directly proportional to the capacitance. Thus, in order to achieve high drain currents with low operational voltages, OTFTs with thin dielectric layers in the channel region are preferred.

The dielectric material may be organic or inorganic. Preferred inorganic materials include $SiO_2$, SiNx and spin-on-glass (SOG). Preferred organic materials are generally polymers and include insulating polymers such as poly vinylalcohol (PVA), polyvinylpyrrolidine (PVP), acrylates such as polymethylmethacrylate (PMMA) and benzocyclobutanes (BCBs) available from Dow Corning. The insulating layer may be formed from a blend of materials or comprise a multi-layered structure.

The dielectric material may be deposited by thermal evaporation, vacuum processing or lamination techniques as are known in the art. Alternatively, the dielectric material may be deposited from solution using, for example, spin coating or ink jet printing techniques and other solution deposition techniques discussed above.

If the dielectric material is deposited from solution onto the organic semiconductor, it should not result in dissolution of the organic semiconductor. Likewise, the dielectric material should not be dissolved if the organic semiconductor is deposited onto it from solution. Techniques to avoid such dissolution include: use of orthogonal solvents for example use of a solvent for deposition of the uppermost layer that does not dissolve the underlying layer; and cross linking of the underlying layer.

The thickness of the insulating layer is preferably less than 2 micrometers, more preferably less than 500 nm.

Organic semiconductors are a class of organic molecules having extensively conjugated pi systems allowing for the movement of electrons.

The performance of organic semiconductors is typically assessed by measurement of its "charge mobility" ($cm^2\,V^{-1}\,s^{-1}$) which may relate to either the mobility of holes or electrons. This measurement relates to the drift velocity of charge carriers to an applied electric field across a material.

Organic semiconductors having relatively high mobilities tend to be those which comprise compounds able to form pi-pi stacks in the solid state. However, the increased level of conjugation required to allow compounds to form such a pi-pi stack also results in a decrease in band gap and stability of the semiconductor, leading to poor performance poor stability. Moreover, these compounds are highly insoluble, which poses particular problems in synthesis and renders their use in efficient transistor production methods, such as ink-jet printing, impossible—see for example San Miguel et al, Org. Lett. 2007, Vol. 9 No. 6 p. 1005 1008.

The present invention seeks to address these problems by providing organic semiconducting materials which combine improved mobility and stability (e.g. stability to atmospheric oxidation) with the solubility required to enable efficient transistor manufacture.

SUMMARY OF THE INVENTION

A first aspect of the present invention relates to a soluble oligomeric compound for forming an organic thin film transistor, the compound having repeat units comprising two or more fused thiophene residues.

The repeat units may, for example comprise the structure

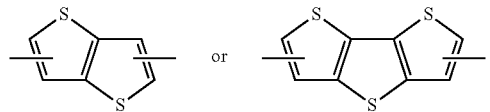

and may be incorporated into the oligomeric backbone via the α position or, alternatively via the β position.

Preferably, the compound comprises two or more terminating groups comprising solvating groups such as planar solvating groups. In some embodiments, the solvating group is selected from optionally substituted straight, branched or cyclic alkyl chains with 1 to 20 carbon atoms, alkoxy, amino, amido, silyl, alkenyl, alkyl and alkylsilyl, preferably alkyl or alkylsilyl. A preferred alkylsilyl solubilising groups comprises trialkylsilylacetylene.

Additionally or alternatively, one or more of the fused thiophene residues may be substituted with a planar solvating group. Preferably, this planar solvating group is selected from the groups listed above.

Preferably the semiconductive compound comprises a structure selected from one of:

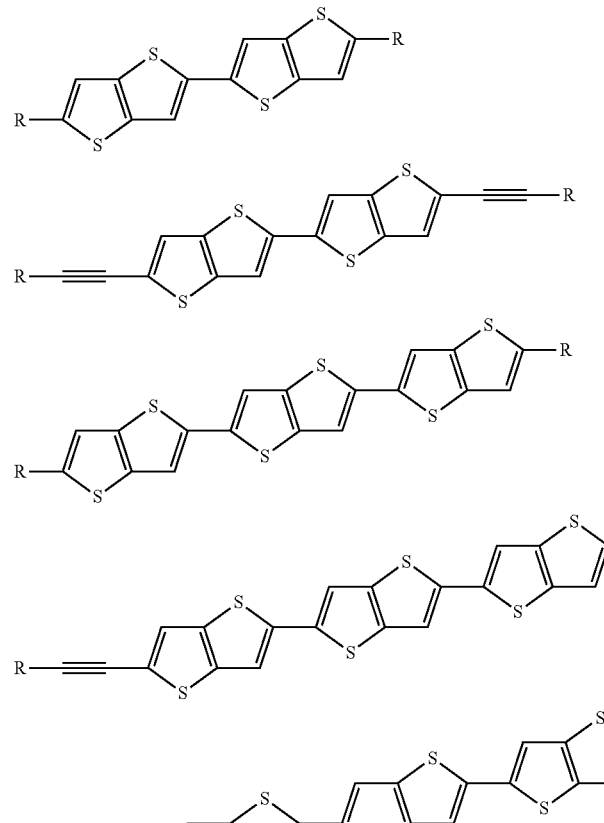

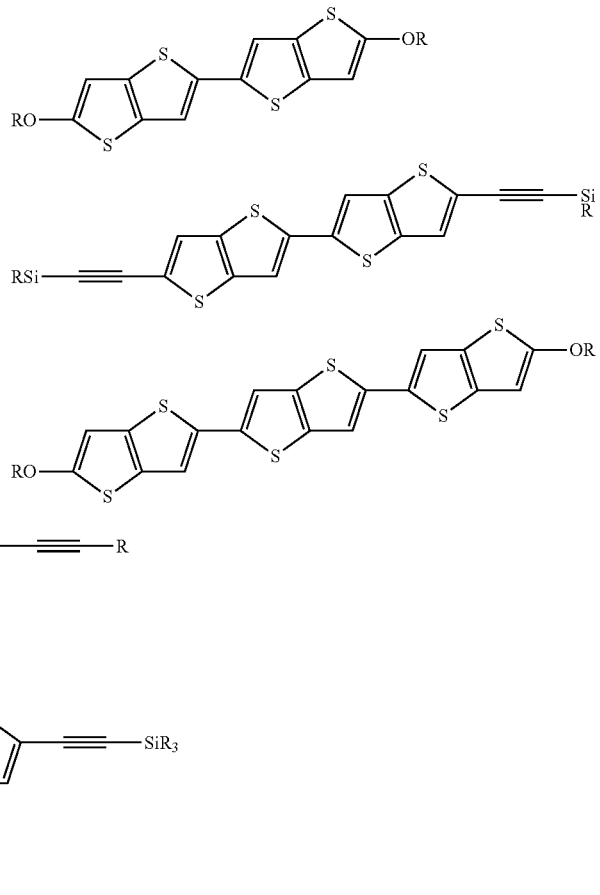

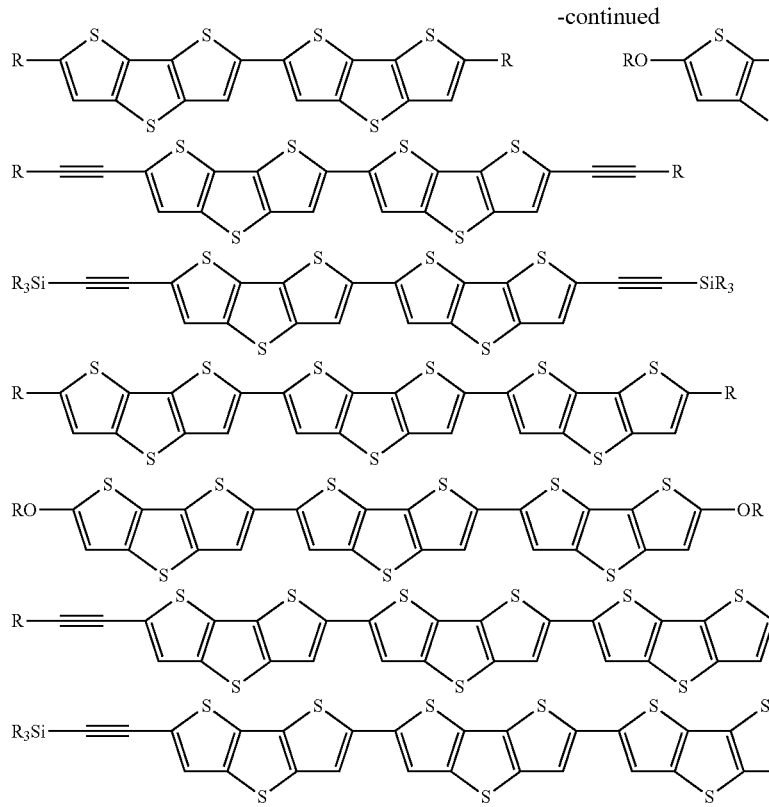
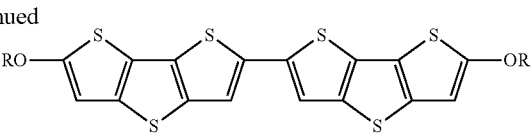

where R forms a solvating group, either alone (as in the first structure above) or in combination with other groups (for example, in combination with an oxygen as shown in the second structure above). R is selected from optionally substituted straight, branched or cyclic alkyl chains with 1 to 20 carbon atoms, alkoxy, amino, amido, silyl, alkenyl, alkyl and alkylsilyl, preferably alkyl or alkylsilyl. R is preferably alkyl.

In a second aspect, the invention relates to a printable solution comprising an oligomeric compound as herein described.

Preferably, the solution comprises the oligomeric compound at a concentration of at least 0.05 molL$^{-1}$, preferably at least 0.5 molL$^{-1}$, most preferably at least 1 molL$^{-1}$ In a third aspect, the invention relates to an organic semiconductor device comprising an oligomeric compound as herein described.

In a fourth aspect, the invention relates to a thin film transistor comprising a semiconductor material as herein described.

In a fifth aspect, the invention relates to an electronic device comprising a thin film transistor as herein described.

In a sixth aspect, the invention relates to a method for manufacturing a thin film transistor comprising ink-jet printing a solution as herein described.

BRIEF DESCRIPTION OF THE FIGURES

Embodiments of the invention will now be described, by way of example only, with reference to the accompanying drawings in which.

DETAILED DESCRIPTION

Figure 1:
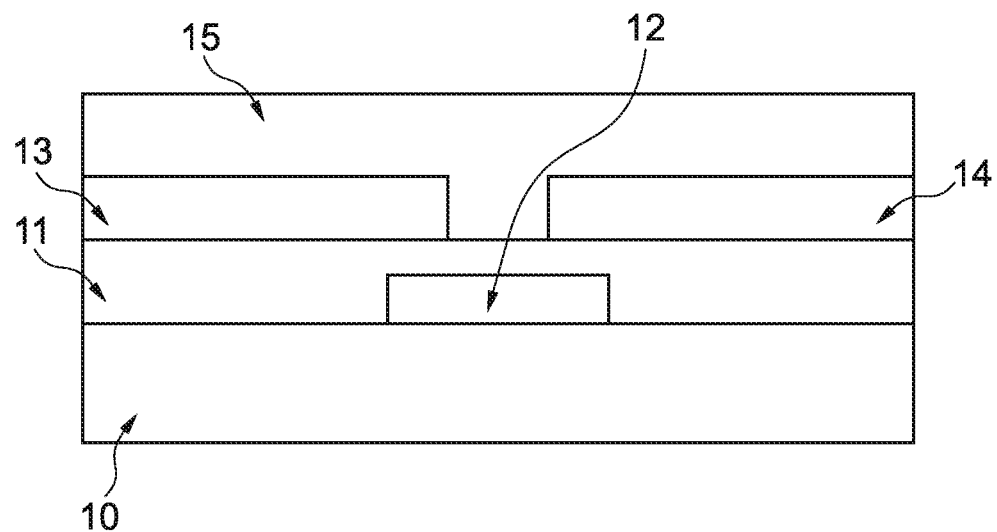
FIG. 1 is a schematic diagram of a general architecture of a bottom-gate organic thin film transistor according to the prior art.

Throughout the following description like reference numerals shall be used to identify like parts.

Organic semiconductors according to embodiments of the present invention may be synthesised as described below.

For example, Compound 1, a soluble dimer of thienothiophene, shown below

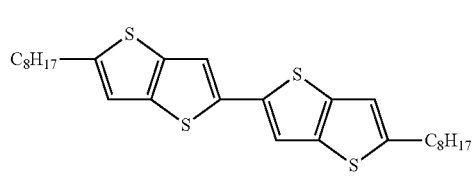

may be synthesized according to the following method:

Intermediate I:

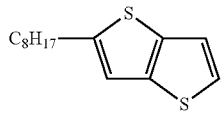

n-Butyllithium (51 ml, 0.14 mol, 2.5M in hexanes) was added drop wise to a solution of thienothiophene (20 g, 0.14 mol) in THF (310 ml) at −78° C. under nitrogen. After stirring at this temperature for 1 hr, octyl bromide (24.9 ml, 0.14 mol) was added drop wise and the reaction mixture allowed to warm to room temperature over night. The mixture was then poured into water, extracted with diethyl ether, dried (MgSO$_4$), filtered and concentrated under reduced pressure. The crude residue was distilled to remove excess bromide and the residue purified by column chromatography (silica gel, hexane) to give the product as a clear oil (15 g, 42.5%).

Compound I

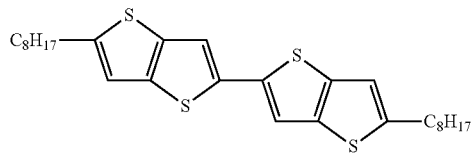

Lithium diisopropylamide (21.8 ml, 39.3 mmol, 1.8M in tetrahydrofuran) was added drop wise to a solution of Intermediate I (9.87 g, 39.2 mmol) in THF at 0° C. under nitrogen. After stirring at this temperature for 1 hr, copper (II) chloride powder (5.32 g, 39.2 mmol) was added portion wise and the reaction mixture allowed to warm to room temperature overnight. It was quenched with water, diluted with dichloromethane and filtered through celite to remove copper residues. The organic phase was washed with water and brine, and dried (MgSO$_4$) and concentrated under reduced pressure. Purification by column chromatography (silica gel, tetrahydrofuran) followed by sublimation gave the product as a yellow solid (582 mg, 5%, (255° C. at $10^{-6}$ Torr)).

For example, Compounds II and III, shown below,

II

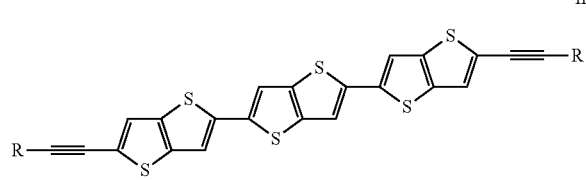

III

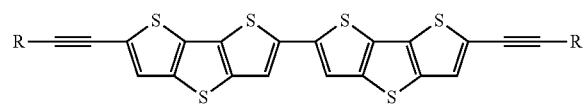

may be synthesised according to a similar method used to synthesise Compound I.

Compound I, II or III is then dissolved in toluene, xylene, tetralin, or chloroform to form a solution of concentration around 1-2 mol L$^{-1}$. This solution may be inkjet printed to provide an effective organic semiconductor (OSC).

Organic semiconductors according to embodiments of the present invention have a wide range of possible applications. One such application is incorporation into an organic thin film transistor (OTFT) to drive pixels in an optical device, preferably an organic optical device. Examples of such optical devices include photoresponsive devices, in particular photodetectors, and light-emissive devices, in particular organic light emitting devices. OTFTs are particularly suited for use with active matrix organic light emitting devices, e.g. for use in displays.

Figure 2:
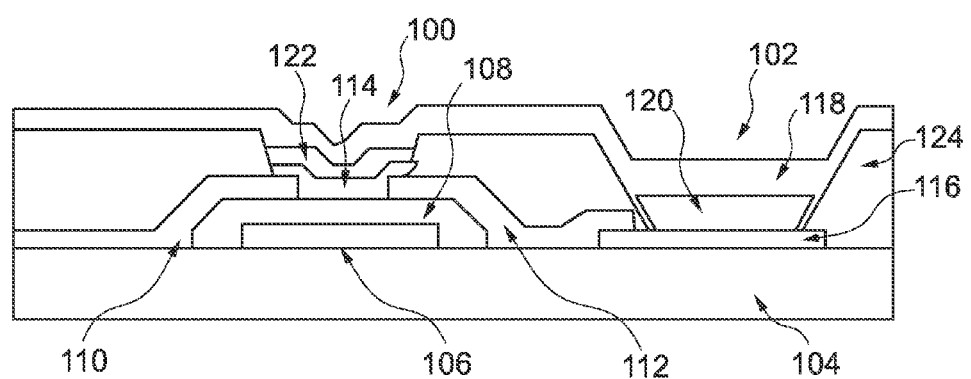
FIG. 2 is a schematic diagram of a pixel comprising an organic thin film transistor and an adjacent organic light emitting device fabricated on a common substrate according to an embodiment of the present invention.

FIG. 2 shows a pixel comprising an organic thin film transistor 100 and an adjacent organic light emitting device (OLED) 102 fabricated on a common substrate 104. The OTFT 100 comprises gate electrode 106, dielectric layer 108, source and drain electrodes 110 and 112 respectively, and OSC layer 114. The OLED 102 comprises anode 116, cathode 118 and an electroluminescent layer 120 provided between the anode 116 and cathode 118. Further layers may be located between the anode 116 and cathode 118, such as charge transporting, charge injecting or charge blocking layers. In the embodiment of FIG. 2, the layer of cathode material 118 extends across both the OTFT 100 and the OLED 102, and an insulating layer 122 is provided to electrically isolate the cathode layer 118 from the OSC layer 114. The active areas of the OTFT 100 and the OLED 102 are defined by a common bank material formed by depositing a layer of photoresist 124 on substrate 104 and patterning it to define OTFT 100 and OLED 102 areas on the substrate.

In FIG. 2, the drain electrode 112 is directly connected to the anode 116 of the organic light emitting device 102 for switching the organic light emitting device 102 between emitting and non-emitting states.

Figure 3:
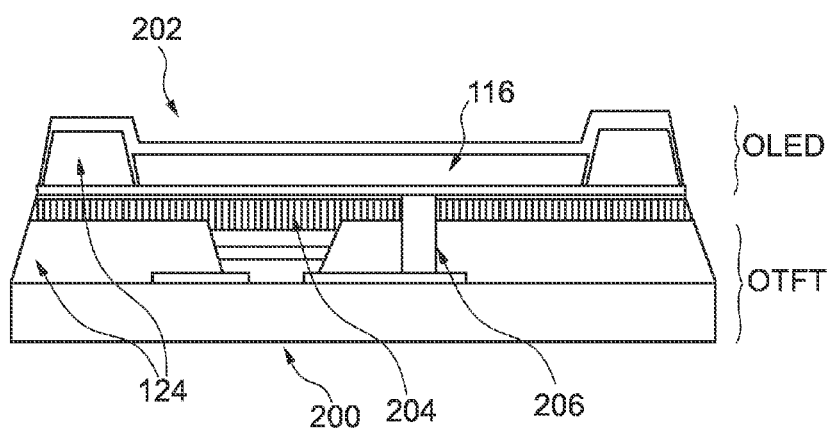
FIG. 3 is a schematic diagram of an organic thin film transistor fabricated in a stacked relationship to an organic light emitting device according to an embodiment of the present invention.

In an alternative arrangement illustrated in FIG. 3, an organic thin film transistor 200 may be fabricated in a stacked relationship to an organic light emitting device 202. In such an embodiment, the organic thin film transistor 202 is built up as described above in either a top or bottom gate configuration. As with the embodiment of FIG. 2, the active areas of the OTFT 200 and OLED 202 are defined by a patterned layer of photoresist 124, however in this stacked arrangement, there are two separate bank layers 124—one for the OLED 202 and one for the OTFT 200. A planarization layer 204 (also known as a passivation layer) is deposited over the OTFT 200. Exemplary passivation layers 204 include BCBs and parylenes. The organic light emitting device 202 is fabricated over the passivation layer 204 and the anode 116 of the organic light emitting device 202 is electrically connected to the drain electrode 112 of the OTFT 200 by a conductive via 206 passing through passivation layer 204 and bank layer 124.

It will be appreciated that pixel circuits comprising an OTFT and an optically active area (e.g. light emitting or light sensing area) may comprise further elements. In particular, the OLED pixel circuits of FIGS. 2 and 3 will typically comprise least one further transistor in addition to the driving transistor shown, and at least one capacitor. It will be appreciated that the organic light emitting devices described herein may be top or bottom-emitting devices. That is, the devices may emit light through either the anode or cathode side of the device. In a transparent device, both the anode and cathode are transparent. It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminium.

Transparent cathodes are particularly advantageous for active matrix devices because emission through a transparent anode in such devices may be at least partially blocked by OTFT drive circuitry located underneath the emissive pixels as can be seen from the embodiment illustrated in FIG. 3.

Thicknesses of the gate electrode, source and drain electrodes may be in the region of 5-200 nm, although typically 50 nm as measured by Atomic Force Microscopy (AFM), for example.

Other layers may be included in the device architecture. For example, in addition to providing a self assembled monolayer (SAM) on the gate, source or drain electrodes one may be provided on the, substrate, insulating layer and organic semiconductor material to promote crystallinity, reduce contact resistance, repair surface characteristics and promote adhesion where required. In particular, the dielectric surface in the channel region may be provided with a monolayer comprising a binding region and an organic region to improve device performance, e.g. by improving the organic semiconductor's morphology (in particular polymer alignment and crystallinity) and covering charge traps, in particular for a high k dielectric surface. Exemplary materials for such a monolayer include chloro- or alkoxy-silanes with long alkyl chains, e.g. octadecyltrichlorosilane.

EXAMPLE 1

Organic field effect transistor devices using Compound I as the active layer were fabricated in a bottom contact device. Devices were fabricated using a 2% solution of chlorobenzene or chloroform, this was filtered through a 0.45 µm filter, and spin coated at 1000 rp/1 sec acc for 60 secs, dried on a hotplate at 100° C. for 5 mins and cooled using a metal block for 1 min.

No doubt many other effective alternatives will occur to the skilled person. It will be understood that the invention is not limited to the described embodiments and encompasses modifications apparent to those skilled in the art lying within the scope of the claims appended hereto.

The invention claimed is:

1. An organic semiconductor comprising a compound selected from the group consisting of:

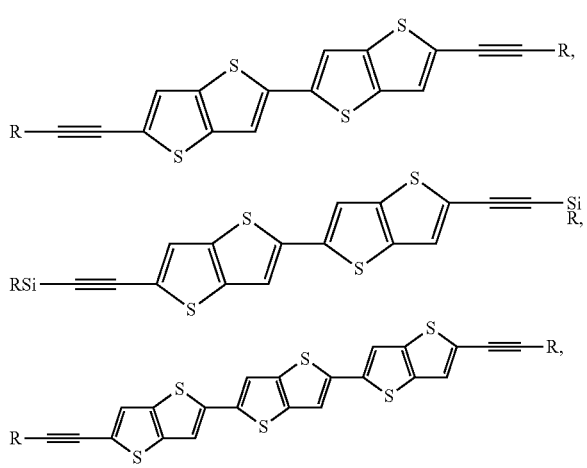

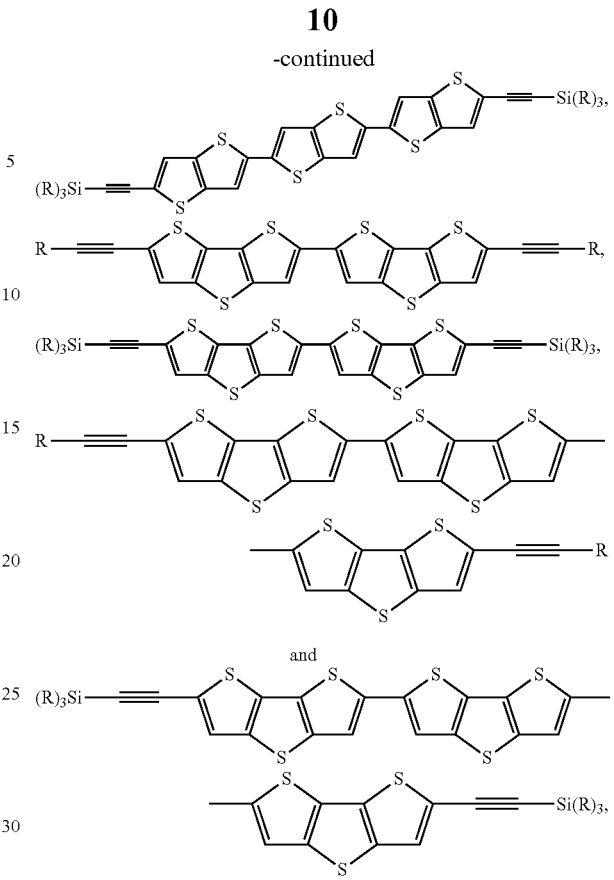

where R is selected from optionally substituted straight, branched or cyclic alkyl chains with 1 to 20 carbon atoms, alkoxy, amino, amido, silyl, alkenyl, alkyl, and alkylsilyl.

2. A printable solution comprising the organic semiconductor according to claim 1.

3. A printable solution according to claim 2, wherein the compound has a concentration of greater than or equal to 1.0 molL$^{-1}$.

4. A thin film transistor comprising the organic semiconductor according to claim 1.

5. An electronic device comprising a thin film transistor according to claim 4.

6. A method for manufacturing a thin film transistor comprising applying a solution according to claim 2 to a substrate, and allowing the solution to solidify.

7. A method according to claim 6 comprising ink-jet printing the solution onto the substrate.

8. The organic semiconductor material according to claim 1, wherein R is alkyl or alkylsilyl.

9. The organic semiconductor material according to claim 1, wherein R is alkyl.

10. The organic semiconductor material according to claim 1, wherein R is alkyl of one carbon atom.

* * * * *